(12) United States Patent
Porat (10) Patent No.: US 6,248,089 B1
(45) Date of Patent: Jun. 19, 2001

(54) TAMPON APPLICATOR

(75) Inventor: Gad Porat, Jerusalem (IL)

(73) Assignee: Medivice Systems Ltd., Jerusalem (IL)

( * ) Notice: Subject to any disclaimer, the term of this patent is extended or adjusted under 35 U.S.C. 154(b) by 0 days.

(21) Appl. No.: 09/391,817

(22) Filed: Sep. 7, 1999

(30) Foreign Application Priority Data

Sep. 7, 1998 (IL) ..................................................... 126111

(51) Int. Cl.⁷ ................................................. A61F 13/20
(52) U.S. Cl. .................................................................. 604/17
(58) Field of Search ........................... 604/11–18, 57–60, 604/285–288, 904

(56) References Cited

U.S. PATENT DOCUMENTS

| | | | |
|---|---|---|---|
| 3,059,641 | * | 10/1962 | Gershen .................................. 604/16 |
| 3,059,642 | * | 10/1962 | Gershen .................................. 604/16 |
| 3,090,385 | * | 5/1963 | Brecht .................................... 604/16 |
| 3,103,929 | * | 9/1963 | Brecht .................................... 604/16 |
| 3,115,876 | * | 12/1963 | Nalle, Jr. ................................ 604/16 |
| 3,297,031 | * | 1/1967 | Bray ....................................... 604/60 |
| 3,831,605 | * | 8/1974 | Fournier ................................. 604/16 |
| 4,769,011 | * | 9/1988 | Swainger ................................ 604/60 |
| 4,900,299 | * | 2/1990 | Webb ..................................... 604/11 |
| 6,019,743 | * | 2/2000 | Cole et al. .............................. 604/15 |

* cited by examiner

*Primary Examiner*—Dennis Ruhl
(74) *Attorney, Agent, or Firm*—Seed IP Law Group PLLC (57) ABSTRACT

A tampon applicator having a housing adapted to accommodate a tampon and a plunger telescopically slidable into the housing at one end thereof to urge the tampon out of the housing at its other end. The plunger is characterized in having a bendably flexible portion so as to enable the plunger to be folded into parallel arrangement with the housing, thereby presenting a compact configuration convenient for packaging and transportation. When required for use, the plunger may unfold, either automatically or manually, to a substantially rectilinear configuration, substantially coaxial with the housing. Once unfolded, the plunger is inserted into the housing a similar manner to existing tampon applicators having a rigid plunger.

19 Claims, 7 Drawing Sheets

TAMPON APPLICATOR

CROSS-REFERENCE TO RELATED APPLICATION

This application claims the benefit of copending Israeli Patent Application No. 126,111, filed Sep. 7, 1998.

TECHNICAL FIELD

The present invention relates to tampon applicators, in particular to tampon applicators which in the packaged configuration are compact and which enable a catamenial tampon to be easily inserted into a woman's vagina.

BACKGROUND OF THE INVENTION

Tampon applicators are well known and are extensively used for inserting catamenial tampons into the vagina during menstruation. Such applicators typically comprise a generally cylindrical housing for the tampon, and a generally cylindrical plunger which is telescopically slidable into the housing. The catamenial tampon is extruded from one end of the housing by sliding or pushing the plunger into the other end of the housing. Since the major portion of the plunger extends out of one end of the housing in preparation for pushing against the tampon within the housing, the length of a tampon applicator in the packaged configuration may be about twice the length of the housing, and several times the length of the actual catamenial tampon. This results in a tampon applicator that is bulky and inconvenient to carry in, for example, a pocket, wallet, purse, pocket book or small handbag, and which is also to some extent fragile, since the plunger may be bent out of alignment with the housing during transportation, rendering the applicator useless, or at best difficult to use.

A number of different approaches have been tried for reducing the overall packaged length of a tampon applicator. One form of compact applicator comprises the plunger and housing as separate components which are assembled by the user typically just prior to use. While perhaps going some way to overcoming the problems of regular telescopic applicators described above, this form of applicator suffers from two major disadvantages, viz., that of non-compliance by a great proportion of potential users, who find the assembly process too time-consuming, fidgety or simply undesirable, and that of the possibility of the plunger being misplaced necessitating a new plunger to be obtained or rendering the applicator useless. Further, the plunger or the housing may be dropped onto a non-hygienic surface such as a floor during assembly, increasing the risk of contamination of these components, particularly when such an assembly is carried out in a bathroom or public lavatory.

Another approach involves an applicator comprising a plunger which is itself formed from a number of elements which telescopically slide one inside the other. In the packaged configuration, the telescopic elements of the plunger are nested one inside the other, offering a compact configuration. When needed for use, a potential user extends the telescopic elements of the plunger which interlock with each other when fully extended, providing a relatively rigid plunger of sufficient length to enable the catamenial tampon to be ejected from the housing. However, this type of applicator is generally expensive to produce, and some users find the plunger extension operation undesirable and/or difficult.

U.S. Pat. No. 3,831,605 discloses yet another type of compact applicator comprising a plunger having a pusher element abutting the tampon, and a thin handle hinged to the pusher element. In the packaged configuration, the handle is situated side-by-side with respect to the housing, and when the applicator is required for use the handle is swiveled about the hinge and locked in longitudinal configuration with respect to the pusher element. A disadvantage of this applicator is that the handle of the plunger is thin and tends to easily bend out of alignment with the housing when the pushing force on the plunger is not perfectly co-axial with the handle, which in practice is the case. Further, the plunger handle may be permanently bent or deformed during the insertion process thereby preventing further actuation of the plunger and resulting in the tampon not being fully ejected from the casing. The locking mechanism between the handle and the pusher element may also be damaged relatively easily during the insertion process thereby enabling the handle to swivel freely about the hinge preventing further ejection of the tampon except with great difficulty. Further, the string for drawing out the tampon extends from the proximal end of the housing during the ejection process, and thus may become entangled with the plunger causing difficulties during tampon insertion into the body, and well as during the subsequent removal of the applicator from the vagina.

One aim of the present invention is to provide a catamenial tampon applicator which overcomes the aforementioned disadvantages of the prior art general applicators and of the prior art compact applicators.

Another aim of the present invention is to provide a compact catamenial tampon applicator which may be operated in a similar manner to regular telescopic applicators.

Another aim of the present invention is to provide a compact catamenial tampon applicator in which the housing and/or plunger may have a curved longitudinal axis.

Another aim of the present invention is to provide a compact catamenial tampon applicator which enables the plunger to be inserted into the housing while maintaining a proximal portion of the plunger at an angle to the longitudinal axis of the housing.

Another aim of the present invention is to provide a compact catamenial tampon applicator which may be inexpensively manufactured.

The present invention achieves these and other aims by providing a compact tampon applicator comprising a housing for the tampon and a telescopically slidable plunger, the plunger being characterized in comprising a bendably flexible portion which enables the plunger to be folded upon itself such that the free end of the plunger is laterally aligned with the housing in the packaged configuration, and enabling the plunger to be unfolded bringing the free end thereof in a proximal relationship with respect to the housing when required for use, thus enabling the plunger to be inserted into the housing thereby ejecting the tampon out of the other end of the housing.

SUMMARY OF THE INVENTION

A tampon applicator, comprising: a housing adapted to accommodate a tampon therein and having a housing distal end, adapted for enabling such a tampon to be ejected therethrough from the housing, and a housing proximal end; a plunger telescopically slidable into said housing through said housing proximal end, said plunger comprising a first portion having tampon abutting end and a second portion comprising a free end; said plunger characterized in comprising bending means intermediate said tampon abutting end and said free end, said bending means being bendably flexible such as to enable the plunger to be flexed and unfolded about at least a portion of said bending means at least from a substantially folded configuration, wherein said second portion is positioned substantially alongside said housing, to a substantially unfolded configuration, wherein said second portion is positioned sufficiently proximally to said housing such as to enable at least a portion of the plunger to be inserted into the housing via said housing proximal end, thereby enabling a tampon that may be accommodated in said housing to be ejected via said distal end.

Preferably, at least a proximal portion of said housing comprises a passageway therethrough which is sized and configured to receive said plunger. The tampon abutting end comprises an enlarged portion of a substantially greater size than that of the said passageway.

In a preferred embodiment said bending means comprises a substantially bellows-like portion having spaced alternating ribs and furrows, said ribs and furrows being substantially extensible and retractable such as to permit the said plunger to be unfolded at least from said folded configuration to said unfolded configuration. In particular, said bending means is substantially resilient, enabling said plunger to be automatically flexed away from said folded configuration at least partially towards said unfolded configuration.

Preferably, said free end of the plunger is substantially tubular. The said bending means is typically comprised intermediate said first portion and said second portion of said plunger, and a longitudinal axis of said second portion is substantially rectilinear.

Optionally, said housing comprises a stepped outer profile comprising a distal enlarged portion, adapted to accommodate a tampon, joined to a proximal smaller grasping portion. The said passageway may then be comprised in said grasping portion. Optionally, said distal end of said housing comprises a number if suitable flexible petals which are capable of bending radially outwards as a tampon is ejected from said housing.

Said enlarged portion may comprise a substantially circular external transverse cross-sectional profile. Similarly, said bending means may comprise a substantially circular external transverse cross-sectional profile. Similarly, said passageway comprises a substantially circular internal transverse cross-sectional profile complementary to the external cross-sectional profile of at least said bending means, though alternatively, said passageway comprises a substantially rectangular internal transverse cross-sectional profile complementary to the external cross-sectional profile of at least said bending means.

Optionally, said applicator further comprising holding means for maintaining the laterally spaced relationship between said second portion and said housing established in the said folded configuration until required by a user. The holding means may comprise a hook-like element located on the outer surface of the said plunger and a corresponding tab, said tab being located on the external surface of the said housing such as to enable the hook-like element to cooperate and engage with the said tab when the plunger is in the said folded configuration. The said hook-like element may be located on the external surface of the plunger such that when the plunger is sufficiently inserted into the housing so as to enable a tampon accommodated therein to be fully ejected therefrom, the said hook-like element abuts the said proximal end of said housing.

The said tampon applicator may thus comprise a suitable catamenial tampon accommodated in said housing, and in particular said tampon may comprise a suitable tampon withdrawal string attached thereto, a free end of said string extending out of said plunger via said aperture.

DETAILED DESCRIPTION OF THE INVENTION

The present invention is defined by the claims, the contents of which are to be read as included within the disclosure of the specification, and will now be described by way of example with reference to the accompanying Figures.

The relative positional terms "proximal" and "distal", respectively designated P and D in the Figures, herein refer to directions away from and towards the body, respectively, unless otherwise specified.

The present invention relates to a compact tampon applicator, generally designated 10, for inserting a catamenial tampon 100 into a woman's vagina during her menstrual period. The tampon 100 comprises a withdrawal string 150 for enabling its removal from the vagina to be effected with minimum discomfort.

With reference to the accompanying Figures, the applicator 10 comprises a housing 20 adapted to accommodate a tampon 100 therein, and a plunger 50. The housing 20 comprises a housing distal end 22, adapted for enabling said tampon 100 to be ejected from the housing through the distal end 22, and a housing proximal end 24. The housing 20 may be substantially tubular, comprising a substantially smooth outer profile. In the preferred embodiment, however, the housing 20 comprises a stepped outer profile, in which the distal enlarged portion 32 of the housing 20 is adapted to accommodate the tampon 100 and is joined to a smaller proximal grasping portion 34. The enlarged portion 32 and the grasping portion 34 each comprise a generally circular external transverse cross-sectional profile, though they may also comprise elliptical or any other suitable transverse cross-sectional profile.

The longitudinal axes 105, 110 of the enlarged portion 32 and the grasping portion 34, respectively, are in the preferred embodiment rectilinear and coaligned. Alternatively, the longitudinal axes 105 and 110 may be curved and have the same or different curvatures. Additionally or alternatively, the longitudinal axes 105 and 110 may be offset or staggered such that, for example, part of the outer surface of the enlarged portion 32 is substantially aligned with a part of the outer surface of the grasping portion 34.

The inner diameter of the enlarged portion 32 is typically just greater than the diameter of the tampon 100 that is to accommodated therein. The grasping portion 34 in the preferred embodiment comprises ribs 38 about the exterior thereof providing a surface which is thereby easier to grasp by the user. Alternatively the exterior surface of said grasping portion 34 may comprise other friction-enhancing means known in the art for facilitating the grasping thereof by a potential user. Optionally, and in the preferred embodiment, the distal end 22 of the housing comprises a number of preferably thin and flexible petals 28 which are capable of bending radially outwards as the tampon 100 is being ejected from the housing 20. The number of petals 28 may be typically three, four, five or more.

The plunger 50 is telescopically slidable into said housing 20 through said housing proximal end 24, in particular the grasping portion 34 of the housing 20. Thus, at least a proximal portion of said housing 20, typically said grasping portion 34, has a passageway 26 therethrough which is sized and configured to receive said plunger 50. The plunger 50 comprises a first portion 51 having a distal tampon abutting end 52, and a second, actuating, portion 53 having a free end 54. At least the longitudinal axis 115 of the first portion 51 is substantially coaligned with the longitudinal axis 110 of the grasping portion 34. Thus, in the preferred embodiment where the axis 110 of the grasping portion 34 is rectilinear, at least the axis 115 of the said first portion 51 is also rectilinear. Alternatively, if the axis 110 of the grasping portion 34 is curved, at least the axis 115 of the said first portion 51 is also curved, and typically comprises the same curvature. In the preferred embodiment, the longitudinal axis 120 of the second portion 53 is rectilinear, but may alternatively be curved, even if the axis 115 of the first portion 51 is not curved or has a different curvature.

The plunger 50 is characterized in comprising bending means 60 intermediate said first and second portions, 51 and 53 respectively, in particular near said first portion 51. The bending means 60 is typically bendably flexible such as to enable or permit the plunger 50 to be flexed or bent and unfolded, preferably reversibly, about at least a portion of said bending means 60 from a first, substantially folded, configuration to a second, unfolded, configuration. In the said folded configuration, the second portion 53 is positioned substantially alongside said housing 20, i.e., substantially laterally aligned therewith, wherein the longitudinal axis 120 of the said second portion 53 is thus laterally spaced from the longitudinal axis 110 of the grasping portion 34 and may be substantially parallel thereto. In the said unfolded configuration, said second portion 53 is positioned sufficiently proximally to said housing 20 such as to enable at least a portion of the plunger to be inserted into the housing 20 via said housing proximal end 24, thereby enabling said tampon 100, accommodated in said housing 20, to be ejected via said distal end 22. Thus, in the said unfolded configuration, the longitudinal axis 120 of said second portion 53 may be at an acute angle or aligned with the longitudinal axis of the said first portion 51, and at least a part of said first portion 51 and said bending means 60 may then be inserted into the casing 20 by pushing the said second portion 53 distally, enabling a tampon 100 accommodated in said housing 20 to be ejected through said housing distal end 22. The said bending means 60 thus enables the longitudinal axis 120 of the second portion 53 to be rotated in relation to the longitudinal axis 115 of the said first portion 51.

In the preferred embodiment, the said bending means 60 is comprised intermediate with, and joined to, the said first and second portions, 51 and 53 respectively, of said plunger 50. The said first portion 51 and second portion 53 are in this case preferably substantially tubular and may each comprise between, for example, 10% to 35% of the length of the plunger 50, the bending means 60 being of sufficient length when flexed to enable the plunger 50 to assume the said folded and unfolded configurations.

Alternatively, the bending means 60 may extend up to the said tampon abutting end 52 and/or free end 54, thereby including said first portion 51 and/or second portion 53, respectively. In other words, the said first portion 51 and/or the second portion 53 may also be of the same form and material as the bending means 60.

The bending means 60 may thus be flexed manually by a user so that the plunger 50 changes configuration from the folded configuration to the unfolded configuration. Optionally, the said changing means 60 may also be resilient, the resilience enabling the plunger 50 to flex and assume the unfolded configuration substantially automatically when the package containing the applicator 10 is opened, as will be described in more detail hereinafter.

In the preferred embodiment, said bending means 60 comprises a substantially bellows-like portion 70 joined to the first portion 51 and second portion 53 of the plunger 50. The bellows-like portion 70 has a number of spaced alternating ribs 72 and furrows 74, said ribs 72 and furrows 74 being preferably resilient and substantially extensible and retractable such as to permit the said bending means 60 to be flexed and unfolded upon itself, preferably reversibly, so as to enable said plunger 50 to be unfolded from said folded configuration to said unfolded configuration.

In order to minimize the tendency of said bellows-like portion 70 to collapse when the plunger 50 is in the second configuration and an actuating pushing force is applied to it, the said bellows-like portion may further comprise one or more longitudinal webs (not shown). Alternatively, the said bellows-like portion may be configured to partially or fully collapse, or buckle, under the said actuating force, wherein the plunger 50 is suitably configured so that its resulting length including the corresponding semi- or fully-collapsed length of the bellows-like portion 70 is still sufficient to fully push the tampon 100 out of the housing 20.

Figure 11:
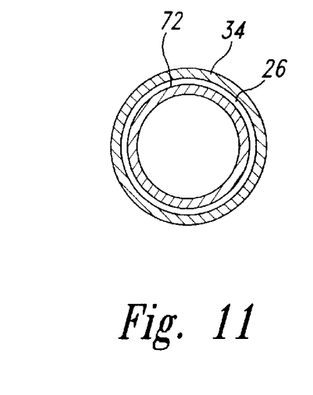
FIG. 11 illustrates a transverse cross-sectional view of the embodiment of FIG. 4 taken along A—A.
Figure 12:
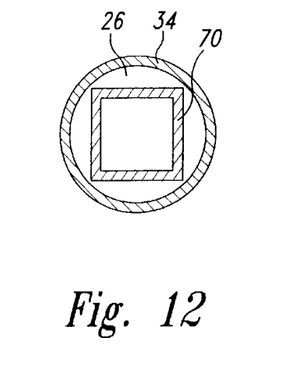
FIG. 12 illustrates, in transverse cross-sectional view, an alternative transverse section of the embodiment of FIG. 4 taken along A—A.
Figure 13:
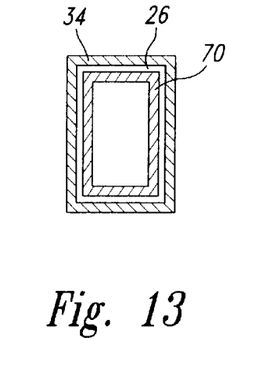
FIG. 13 illustrates, in transverse cross-sectional view, an alternative transverse section of the embodiment of FIG. 4 taken along A—A.
Figure 14:
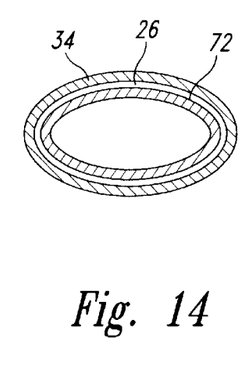
FIG. 14 illustrates, in transverse cross-sectional view, an alternative transverse section of the embodiment of FIG. 4 taken along A—A.

The said bending means 60 may comprise a substantially circular, elliptical, rectangular or any other suitable external transverse cross-sectional profile. For example, and as shown in FIG. 11 for the first embodiment of the present invention, the external transverse cross-sectional profile of the bellows-like portion 70 may be substantially circular, such that the outer diameter of the ribs 72 is slightly smaller than the inner diameter of the passageway 26. In such a case, the said passageway 26 comprises a substantially circular internal cross-sectional profile complementary to the external transverse cross-sectional profile of at least the ribs 72. Alternatively the bellows-like portion 70 may have a rectangular cross-section, optionally comprising rounded edges, wherein the passageway 26 is of circular cross section and sized to circumscribe the rectangular profile of the said ribs 72, or alternatively the passageway is of a complementary rectangular internal transverse cross-sectional profile, as illustrated in FIGS. 12 and 13, respectively. In fact, the embodiment shown in FIG. 13 shows an external rectangular transverse cross-sectional profile for the grasping portion 34, though alternatively the external surface of the grasping portion 34 may remain substantially cylindrical. Alternatively, and as shown in FIG. 14, the bellows-like portion 70 and the passageway 26 may comprise complementary elliptical transverse cross-sectional profiles. The transverse cross-sectional profile of said flexible portion 80 of the second embodiment of the present invention may be similarly circular, rectangular or elliptical, as described hereinbefore regarding the said bellows-like portion 70 of the first embodiment, in particular with respect to the transverse cross-sectional profiles of the said passageway 26 and of the grasping position 34, mutatis mutandis.

A substantially non-circular transverse cross-section for the said bellows-like portion 70 helps maintain the unfolding motion of the bending means 60 from the first configuration to the second configuration substantially along a plane.

Figure 7:
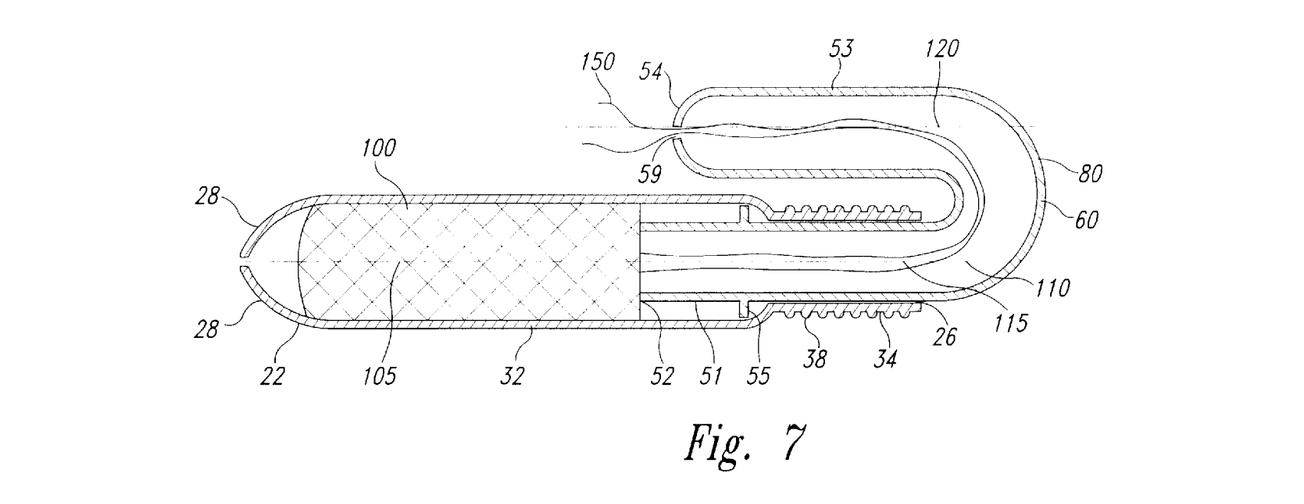
FIG. 7 illustrates, in longitudinal cross-sectional view, the structural characteristics of a second embodiment of the present invention in the packaged configuration.
Figure 8:
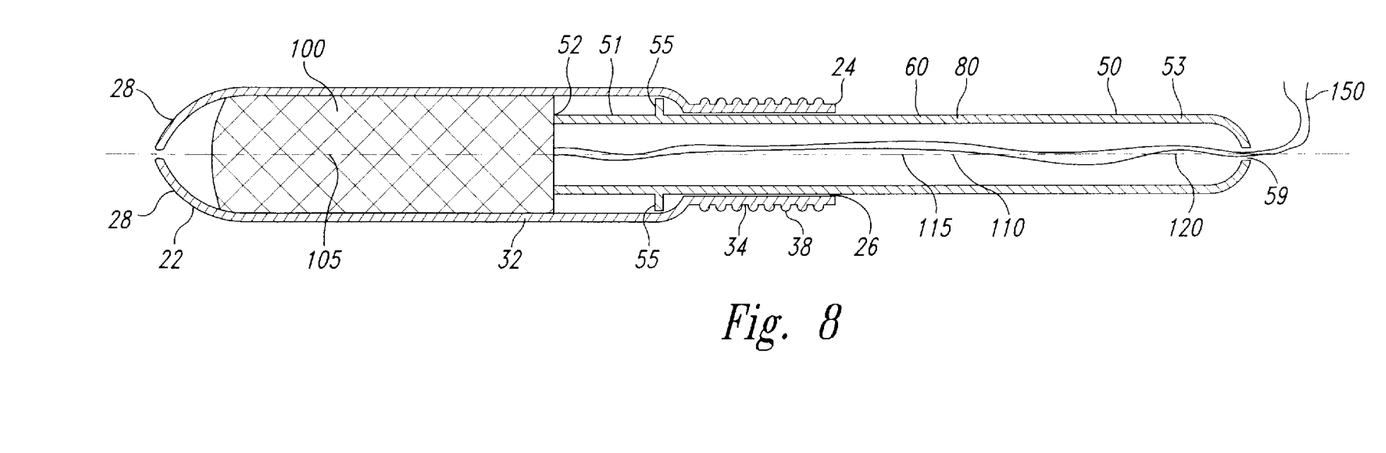
FIG. 8 illustrates the embodiment of FIG. 7 in the ready for use configuration.

Alternatively, and as illustrated in FIGS. 7 and 8 for the second embodiment of the present invention, the said bending means 60 may comprise a suitable flexible portion 80, such as a length of flexible tubing comprising a substantially circular, elliptical, rectangular or any other suitable cross-section, and joined to said first portion 51 and second portion 53 of the plunger 50. The flexible portion 80 is suitably flexible such as to permit the said plunger 50 to be unfolded at least from said unfolded configuration to said folded configuration. The said flexible portion 80 may be comprised, for example, from a material that is inherently flexible, such as latex or rubber, for example, and formed into a suitable shape, for example tubular. The flexibility of the flexible portion 80 enables the same to be folded upon itself for permitting the plunger 50 to assume the said folded configuration, wherein the flexible portion 80 thereby assumes, for example, a flattened transverse cross-section. Optionally, the said flexible portion 80 may further be resilient, and also enables the said free end 54 of the plunger 50 to assume at more-or-less proximal configuration with respect to the housing 20 as the flexible portion 80 springs back bringing the plunger 50 into the unfolded configuration. The said flexible portion 80 may advantageously comprise one or more longitudinal ribs (not shown) along the outer or inner surface thereof to enhance the longitudinal stiffness of the flexible portion 80 and thus prevent it from collapsing or buckling under the action of a longitudinal force that pushes the plunger 50 into the housing 20.

The plunger free end 54 may be substantially tubular, the lumen of which is in communication with the exterior of the applicator 10 as well as the interior of the housing 20, and thus provides a path to the exterior of the applicator 10 for the withdrawal string 150.

Figure 17:
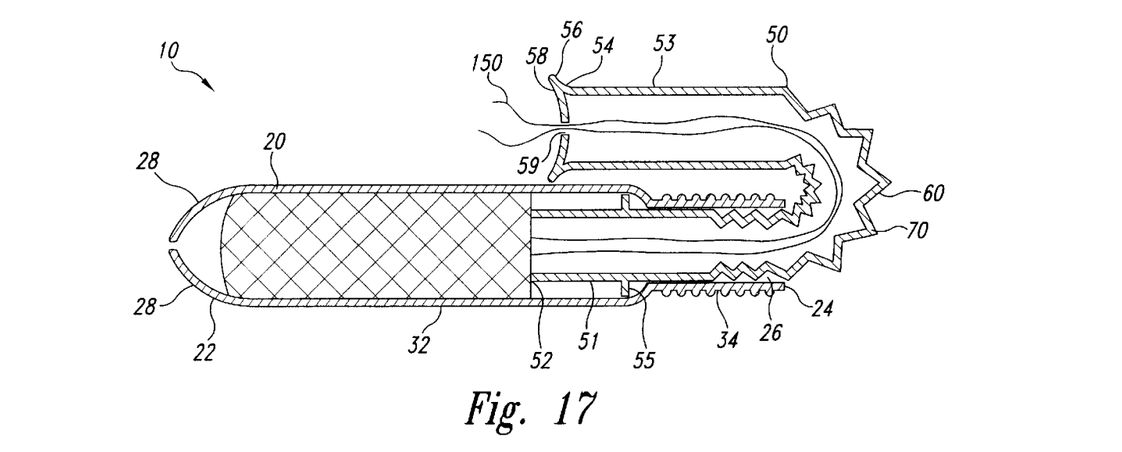
FIG. 17 illustrates the embodiment of FIG. 3 comprising an alternative plunger free end.
Figure 18:
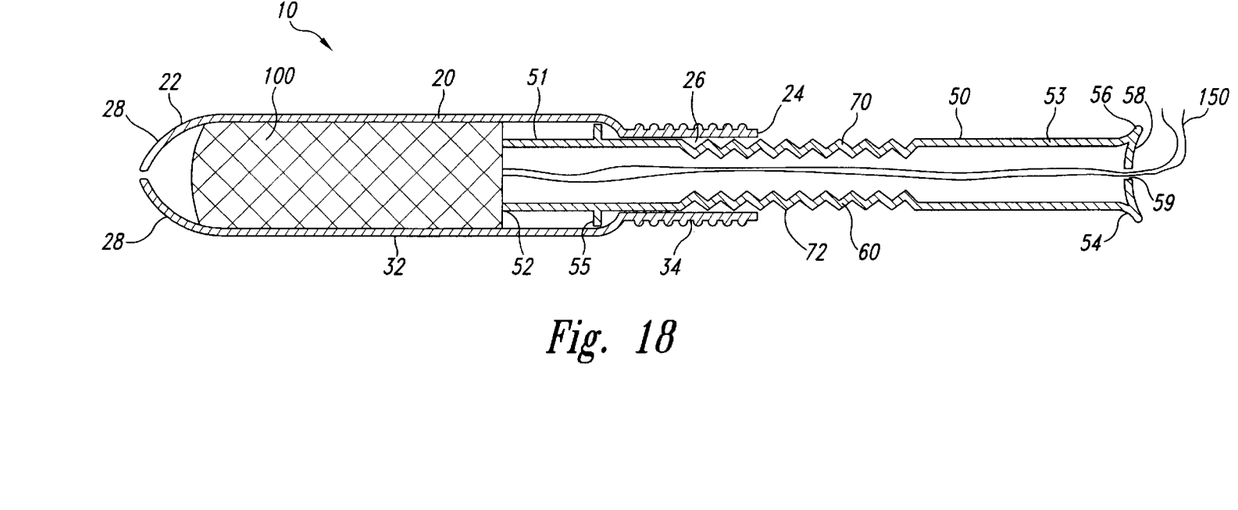
FIG. 18 illustrates the embodiment of FIG. 4 comprising an alternative plunger free end.

Alternatively, the plunger free end 54 is convex and also smoothly rounded, presenting a smooth surface onto which the actuating finger, typically the index finger, of the user may press when pushing the plunger 50 into the housing 20, as illustrated in FIGS. 1 to 10 and 15. Alternatively, The plunger free end 54 may comprise an enlarged portion 56 having a diameter greater than that of the housing proximal end 24 or at least greater than the diameter of the said passageway 26, and comprises a concave proximal profile 58 as illustrated in FIGS. 17 and 18. The enlarged portion 56 acts as a stop and prevents the plunger 50 being inserted too far inside the housing 20, and thus minimizes any risk of inserting the plunger 50 into the vagina itself The concave profile 58 is generally complementary to the profile of the tip of the index finger which is usually used for pushing the plunger 50 into the housing 20, and thus provides a user with greater traction thereat, increasing her confidence in using the applicator 10. Preferably, the said free end 54 comprises an aperture 59 suitably sized to enable the said withdrawal string 150 to be threaded therethrough from inside the housing 20 and plunger 50, and out thereof.

Figure 15:
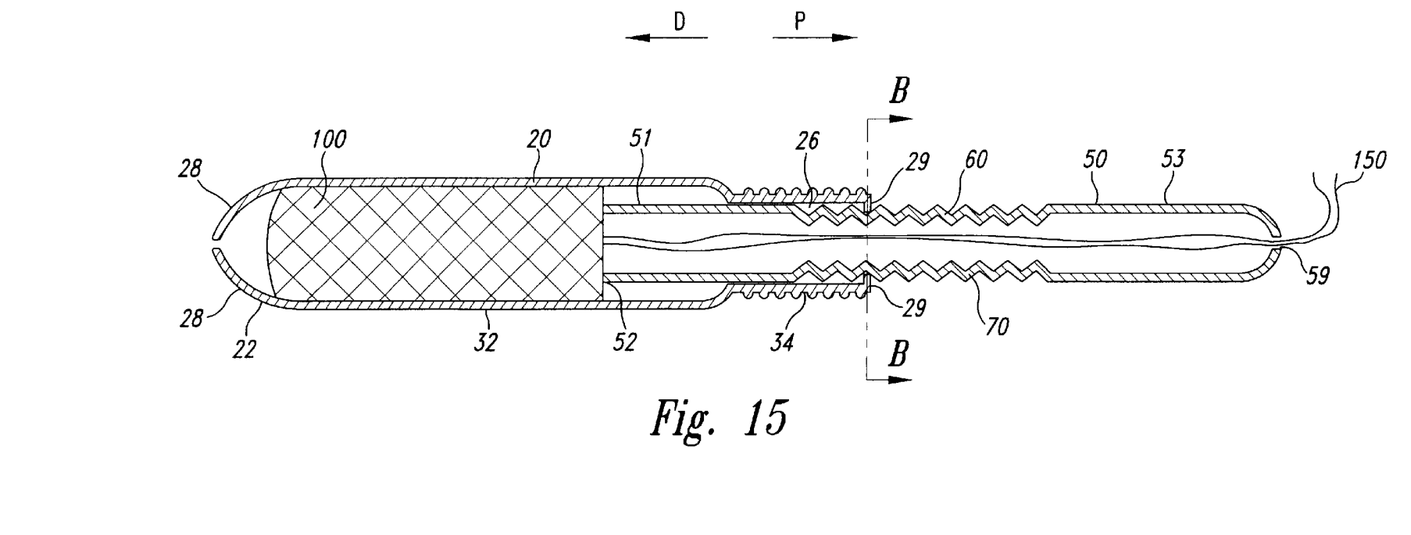
FIG. 15 illustrates a different aspect of the embodiment of FIG. 4.
Figure 16:
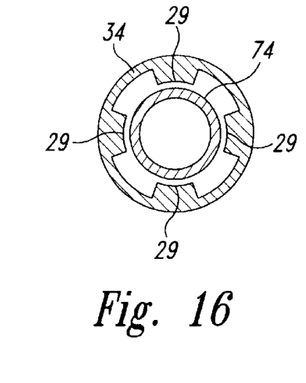
FIG. 16 illustrates a transverse cross-sectional view of the embodiment of FIG. 15 taken along B—B.

The tampon abutting end 52 preferably comprises a flared or enlarged portion 55 preferably proximal thereto, being of a substantially larger size than the said passageway 26, thereby preventing the plunger from accidentally falling out of the housing 20 proximally. Alternatively, and as illustrated in FIGS. 15 and 16, in another aspect of the present invention, the plunger 50 may be substantially prevented from accidentally falling out of the housing 20 by providing inwardly extending projections 29 at the said proximal end 24 of the housing 20, said projections 29 being adapted to engage with the furrows 74 of the bellows-like portion 70. Since the ribs 72 and furrows 74 of the bellows-like portion 70 are flexible, and preferably also resilient, they may be deformed temporarily by contact with the projections 29 to enable the plunger 50 to be fully inserted into the housing 20.

The tampon applicator 10 of the present invention is typically packed or packaged with the said plunger 50 in the said folded configuration, and thus presents a relatively compact volume. The individual packaging means for each applicator 10 is preferably made from a material that enables the applicator 10 to be hygienically wrapped and protected from accidental opening, and should be configured to prevent the plunger from accidentally flexing away from the folded configuration while packaged. Optionally, the applicator 10 may comprise holding means for maintaining the laterally spaced relationship between the said second portion 53 and the said housing 20 established in the said folded configuration, and thus prevent accidental unfolding of the plunger 50 until the said applicator 10 is required by a user. In the preferred embodiment, said holding means comprise a tab or projection 80 located on the outer surface of the housing 20 and a cooperating hook-like member 82 on the outer surface of the plunger. Thus, with the plunger in the folded configuration, the hook-like member engages with the tab, and thus retains the plunger 50 in the said first configuration. The hook-like member may be easily disengaged from the tab when the applicator 10 is required for use. Advantageously, the hook-like member is strategically located on the plunger 50 such that it also acts as a stop. Thus, the extent to which the plunger 50 may be inserted into the housing 20 may be limited by the hook-like member, which abuts the said proximal end 24 of the housing 20, and thus prevents accidental insertion of the whole plunger 50 into the housing 20, which is at the very least undesirable.

The housing 20 may be made, for example, from at least one layer of paper or cardboard, or alternatively from a thermoplastic plastic using injection or extrusion molding techniques, as is known in the art. Typically, the said plunger 50 may be manufactured, for example, as a vacuumed-formed, injection-molded or extrusion-molded plastic component. The plunger 50 of the second embodiment may be manufactured, for example, by mounting a flexible means 80 such as a suitable rubber hose onto two plastic end pieces suitably shaped to comprise said first and second portions 51 and 53, respectively. Alternatively, the plunger 50 of the second embodiment may be made from a single piece of suitably shaped rubber hose.

Figure 1:
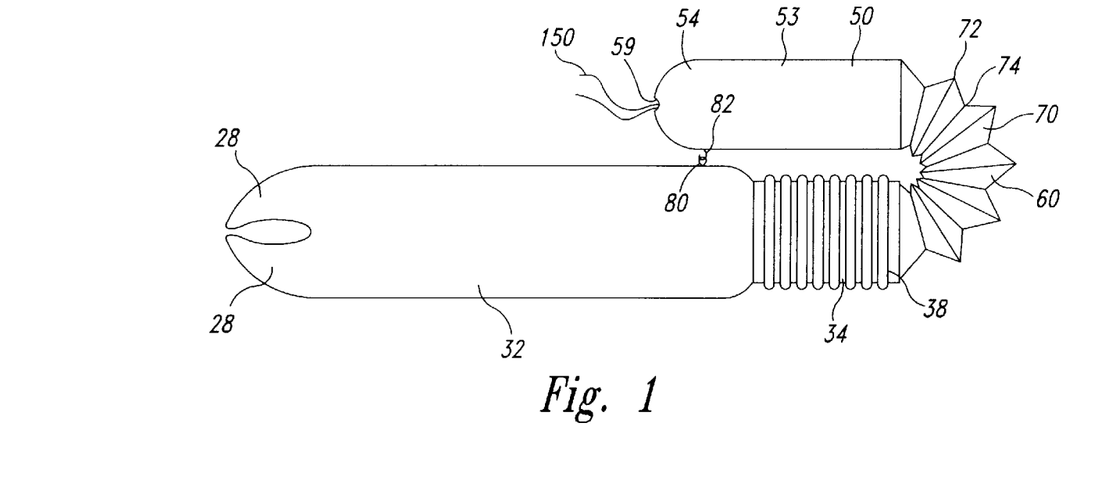
FIG. 1 illustrates, in side view, the structural characteristics of a preferred embodiment of the present invention in the packaged configuration.
Figure 2:
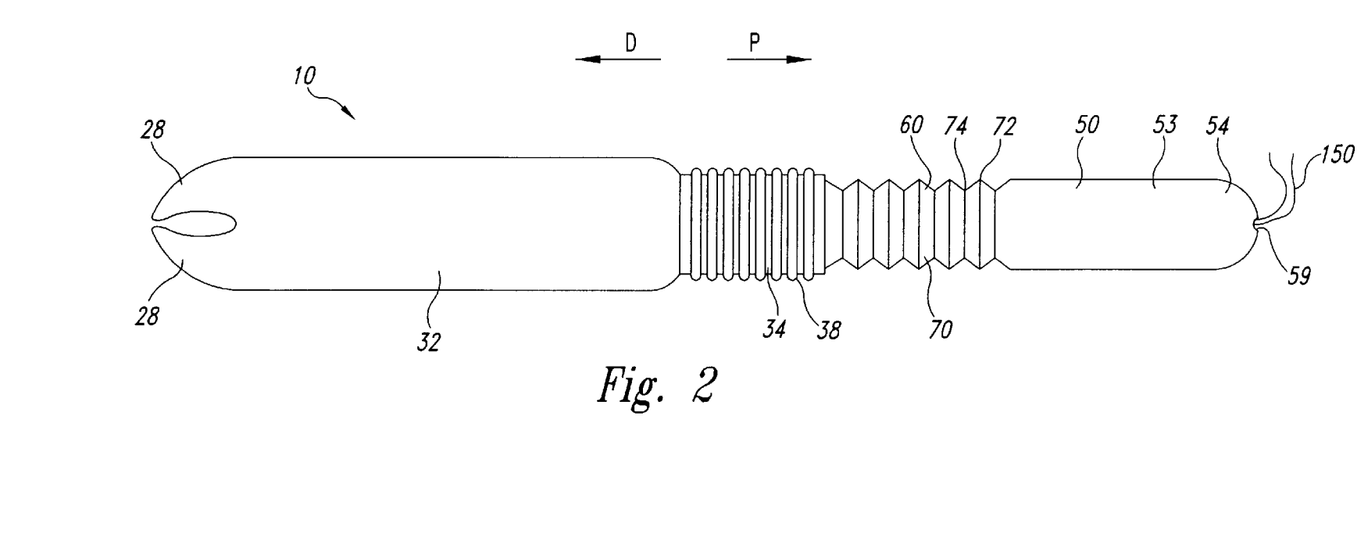
FIG. 2 illustrates the embodiment of FIG. 1 in the ready for use configuration.
Figure 3:
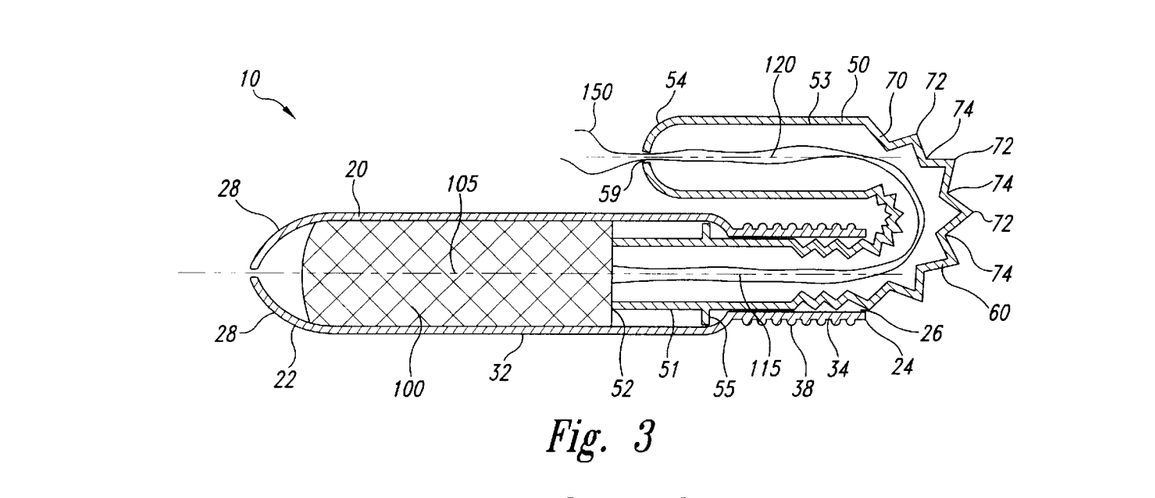
FIG. 3 illustrates the embodiment of FIG. 1 in longitudinal cross-sectional view.
Figure 4:
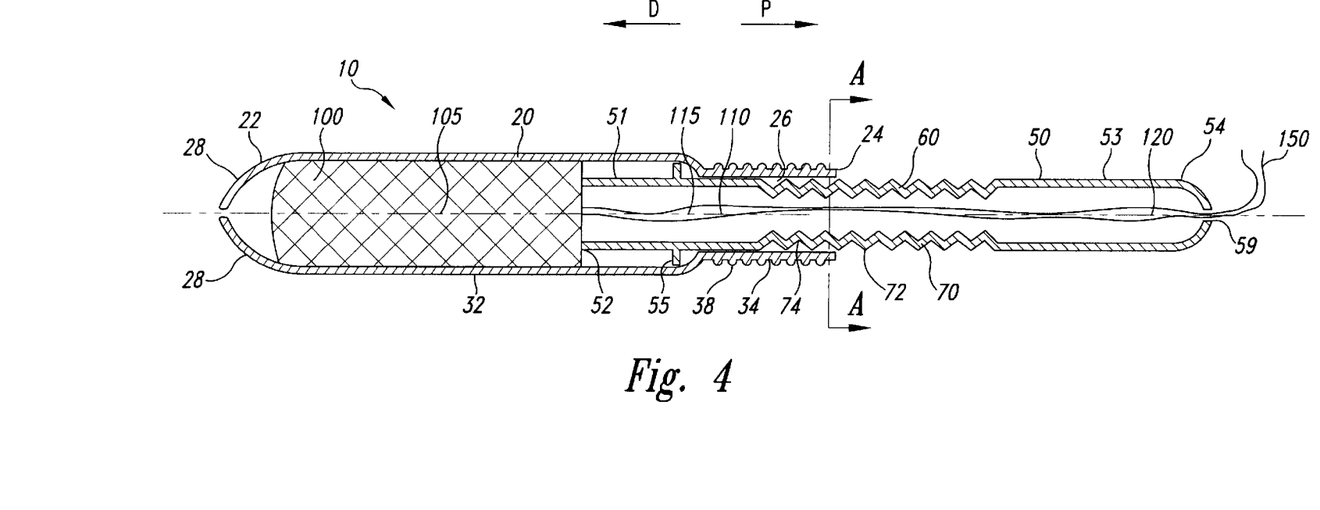
FIG. 4 illustrates the embodiment of FIG. 2 in longitudinal cross-sectional view.
Figure 5:
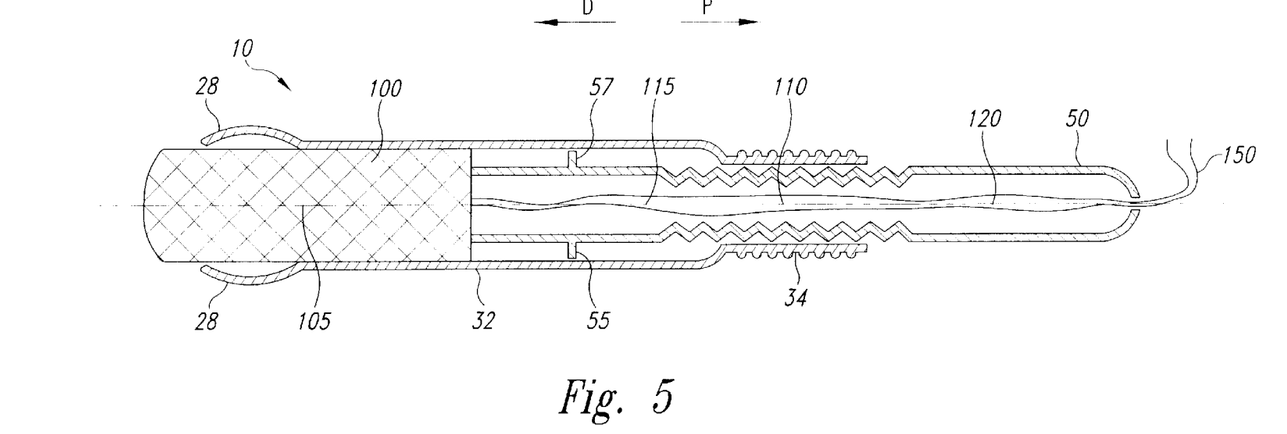
FIG. 5 illustrates the embodiment of FIG. 4 during actuation thereof
Figure 6:
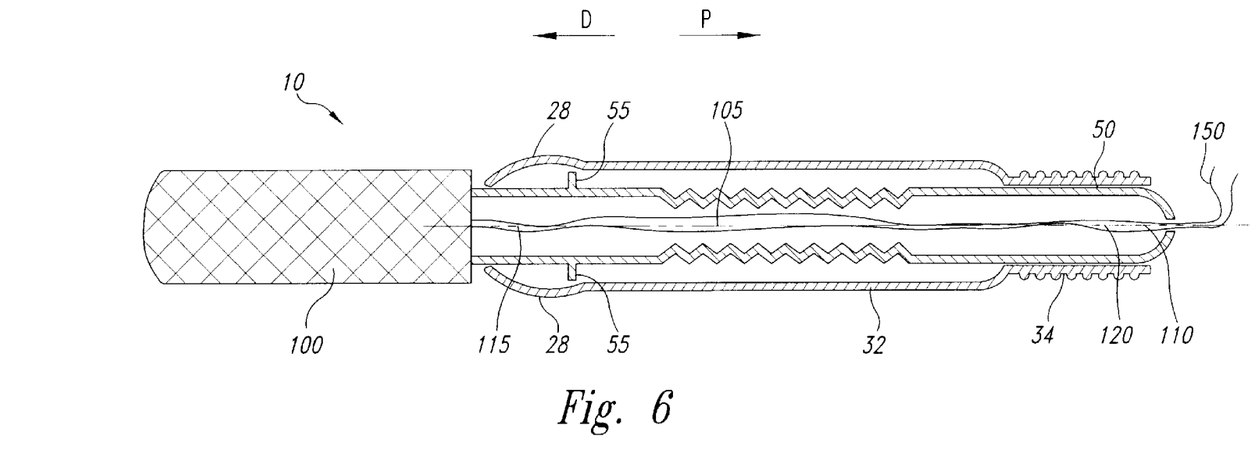
FIG. 6 illustrates the embodiment of FIGS. 4 and 5 at the end of actuation thereof.

The said applicator 10 may be used as follows. A user opens a new tampon applicator packet containing said applicator 10 as shown in FIGS. 1 and 2 (or FIG. 7). The plunger 50 may automatically unfold from the folded configuration to the unfolded configuration, where the bending means 60 is resilient, or alternatively, the hook-like element is first disengaged from the tab, when these are provided. The user may then further flex and unfold the bending means 60. Alternatively, where the bending means 60 is not resilient, the bending means 60 is manually flexed and fully or partially unfolded to bring the free end 54 in a proximal relationship with respect to the housing 20. In one method of use, the longitudinal axis 120 of the second portion 53 is aligned with the longitudinal axis 115 of the first portion 51 (FIG. 4; FIG. 8), and the plunger 50 is then slid distally into the housing 20 via said proximal end 24 and said passageway 26, typically by the user grasping the grasping portion 34 with the thumb and middle finger, and pushing the plunger 50 distally with the index finger. As the plunger 50 is inserted, the tampon abutting end 52 pushes against the tampon 100, ejecting it from the housing 20 while the petals 28 are radially pushed out by the ejecting action (FIG. 5). When the tampon 100 is fully ejected from the housing 20 (FIG. 6), the applicator 10 may be removed, leaving the withdrawal string 150 attached to the tampon 100.

Figure 9:
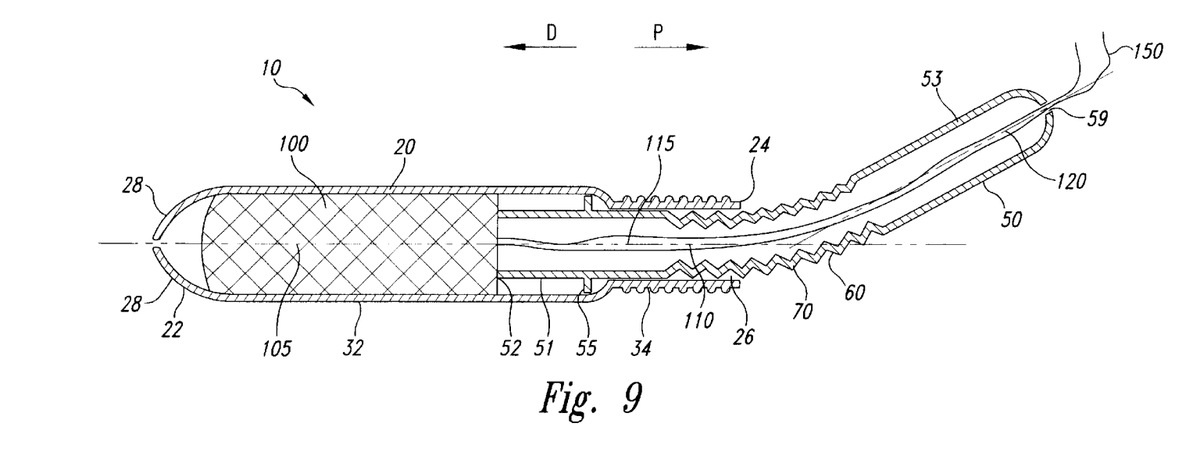
FIG. 9 illustrates the embodiment of FIG. 4 used in a different manner.
Figure 10:
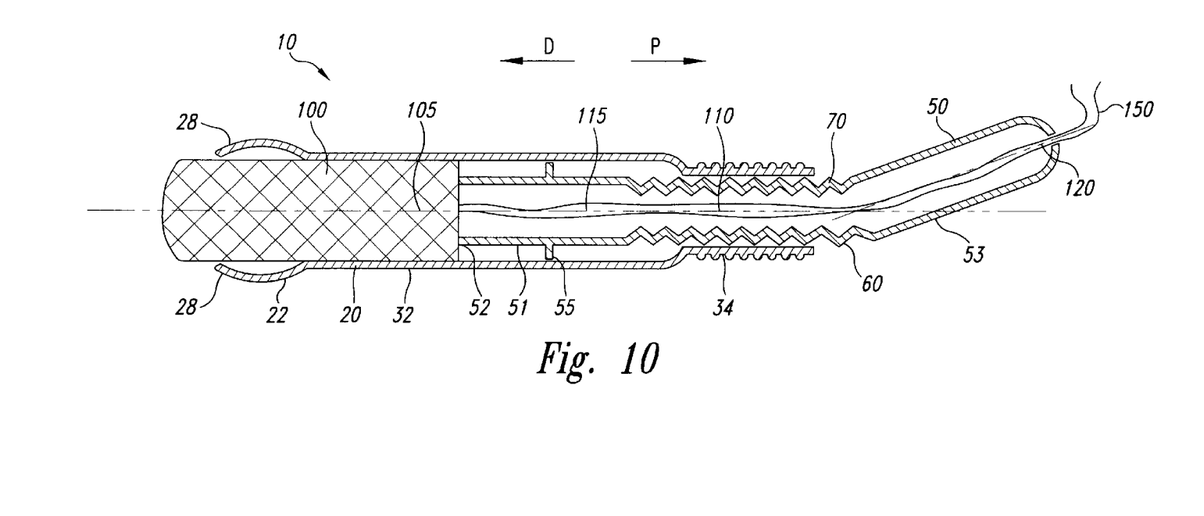
FIG. 10 illustrates the embodiment of FIG. 5 used in a different manner.

In a different method of use, when the plunger 50 is unfolded from the folded configuration to the unfolded configuration, the longitudinal axis 120 of the second portion 53 lies at an angle greater than 0°, but less than 90°, to the longitudinal axis 115 of the first portion 51, as illustrated in FIG. 9 for the first embodiment of the present invention, for example. In this position, some users may find it easier to manipulate and insert the plunger 50 into the housing 20, until the proximal end of the bending means 60 reaches the proximal end 24 of the housing 20, as illustrated in FIG. 10, for example. At this point, the second portion 53 is flexed some more about the bending means 60 until the longitudinal axis 120 of the second portion 53 is aligned with the longitudinal axis 110 of the grasping portion 34, enabling at least part of the second portion 53 to be inserted into the housing 20 for fully expelling the tampon 100 therefrom.

As described hereinbefore, the longitudinal axis 120 of the second portion 53 may be curved. In such an embodiment, the curved longitudinal axis 120 may be considered as an arc of a circle, the arc having the arcuate length of the said second portion 53, and defining a corresponding chord. Thus, the chord of the arc corresponding to the said longitudinal axis 120 of said second portion 53 may be aligned with, or alternatively set at an angle substantially greater than zero with respect to, a longitudinal axis 110 of at least a proximal portion of the housing 20, typically of the grasping portion 34. Such an applicator may be used in a similar manner to that described in the above methods of use for an applicator comprising a rectilinear second portion 53, mutatis mutandis.

While in the foregoing description describes in detail only a few specific embodiments of the invention, it will be understood by those skilled in the art that the invention is not limited thereto and that other variations in form and details may be possible without departing from the scope and spirit of the invention herein disclosed.

What is claimed is:

1. A tampon applicator, comprising:
    a housing adapted to accommodate a tampon therein and having a housing distal end, adapted for enabling such a tampon to be ejected therethrough from the housing, and a housing proximal end;
    a plunger telescopically slidable with respect to said housing, said plunger comprising a first portion having tampon abutting end and a second portion comprising a free end;
    said plunger characterized in comprising bending means intermediate said tampon abutting end and said free end, said bending means being bendably flexible such as to enable the plunger to be flexed and unfolded about at least a portion of said bending means at least from a substantially folded configuration, wherein said second portion is positioned substantially alongside said housing and moved into a substantially unfolded configuration, wherein said second portion is positioned in the substantially unfolded configuration sufficiently proximally to said housing such as to enable at least a portion of the plunger to be inserted into the housing via said housing proximal end, thereby enabling a tampon that may be accommodated in said housing to be ejected via said distal end, said bending means comprises a substantially bellows-like portion having spaced alternating ribs and furrows, said ribs and furrows being substantially extensible and retractable such as to permit the said plunger to be unfolded at least from said folded configuration to said unfolded configuration.

2. A tampon applicator as claimed in claim 1 wherein at least a proximal portion of said housing comprises a passageway therethrough which is sized and configured to receive at least a portion of said plunger.

3. A tampon applicator as claimed in claim 2 wherein said tampon abutting end comprises an enlarged portion of a substantially greater size than that of the said passageway.

4. A tampon applicator as claimed in claim 2 wherein said passageway comprises a substantially circular internal transverse cross-sectional profile complementary to an external cross-sectional profile of at least said bending means.

5. A tampon applicator as claimed in claim 2 wherein said passageway comprises a substantially rectangular internal transverse cross-sectional profile complementary to an external cross-sectional profile of at least said bending means.

6. A tampon applicator as claimed in claim 1 wherein said housing comprises a stepped outer profile comprising a distal enlarged portion, adapted to accommodate a tampon, joined to a proximal smaller grasping portion.

7. A tampon applicator as claimed in claim 6 wherein said passageway is comprised in said grasping portion.

8. A tampon applicator as claimed in claim 6 wherein at least said enlarged portion comprises a substantially circular external transverse cross-sectional profile.

9. A tampon applicator as claimed in claim 1, further comprising holding means for maintaining the laterally spaced relationship between said second portion and said housing established in the said folded configuration until required by a user.

10. A tampon applicator as claimed in claim 9 wherein said holding means comprises a hook-like element located on an outer surface of the said plunger and a corresponding tab, said tab being located on an external surface of the said housing such as to enable the hook-like element to cooperate and engage with the said tab when the plunger is in the said folded configuration.

11. A tampon applicator as claimed in claim 17 wherein said hook-like element is located on the external surface of the plunger such that when the plunger is sufficiently inserted into the housing so as to enable a tampon accommodated therein to be ejected therefrom, the said hook-like element abuts the said proximal end of said housing.

12. A tampon applicator as claimed in claim 1 wherein said bending means is substantially resilient, enabling said plunger to be automatically flexed away from said folded configuration at least partially towards said unfolded configuration.

13. A tampon applicator as claimed in claim 1 wherein said free end is substantially tubular.

14. A tampon applicator as claimed in claim 1 wherein said bending means is comprised intermediate said first portion and said second portion of said plunger.

15. A tampon applicator as claimed in claim 1 wherein a longitudinal axis of said second portion is substantially rectilinear.

16. A tampon applicator as claimed in claim 1 wherein said distal end of said housing comprises a number of flexible petals which are capable of bending radially outwards as a tampon is ejected from said housing.

17. A tampon applicator as claimed in claim 1 wherein at least said bending means comprises a substantially circular external transverse cross-sectional profile.

18. A tampon assembly comprising:

a housing adapted to accommodate a tampon therein and having a housing distal end, adapted for enabling such a tampon to be ejected therethrough from the housing, and a housing proximal end;

a suitable catamenial tampon accommodated in said housing;

a plunger telescopically slidable with respect to said housing, said plunger comprising a first portion having tampon abutting end and a second portion comprising a free end;

said plunger characterized in comprising bending means intermediate said tampon abutting end and said free end, said bending means being bendably flexible such as to enable the plunger to be flexed and unfolded about at least a portion of said bending means at least from a substantially folded configuration, wherein said second portion is positioned substantially alongside said housing and moved into a substantially unfolded configuration, wherein said second portion is positioned in the substantially unfolded configuration sufficiently proximally to said housing such as to enable at least a portion of the plunger to be inserted into the housing via said housing proximal end, thereby enabling the tampon accommodated in said housing to be ejected via said distal end, said bending means comprises a substantially bellows-like portion having spaced alternating ribs and furrows, said ribs and furrows being substantially extensible and retractable such as to permit the said plunger to be unfolded at least from said folded configuration to said unfolded configuration.

19. A tampon applicator as claimed in claim 18 wherein said tampon comprises a tampon withdrawal string attached thereto, a free end of said string extending out of said plunger via an aperture.

\* \* \* \* \*

UNITED STATES PATENT AND TRADEMARK OFFICE
CERTIFICATE OF CORRECTION

PATENT NO. : 6,248,089 B1
DATED : June 19, 2001
INVENTOR(S) : Gad Porat

It is certified that error appears in the above-identified patent and that said Letters Patent is hereby corrected as shown below:

Column 11, claim 11,
Line 8, "claimed in claim 17" should read -- claimed in claim 10 --.
Line 12, "to be ejected therefrom," should read -- to be fully ejected therefrom, --.

Signed and Sealed this

Nineteenth Day of February, 2002

Attest:

Attesting Officer

JAMES E. ROGAN
Director of the United States Patent and Trademark Office